US010203844B2

(12) United States Patent
Baba

(10) Patent No.: US 10,203,844 B2
(45) Date of Patent: Feb. 12, 2019

(54) INFORMATION PROCESSING APPARATUS, INFORMATION PROCESSING SYSTEM, AND METHOD

(71) Applicant: Ryoichi Baba, Tokyo (JP)

(72) Inventor: Ryoichi Baba, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 474 days.

(21) Appl. No.: 15/075,662

(22) Filed: Mar. 21, 2016

(65) Prior Publication Data
US 2016/0274745 A1 Sep. 22, 2016

(30) Foreign Application Priority Data

Mar. 20, 2015 (JP) ................. 2015-057765

(51) Int. Cl.
*G06F 3/0482* (2013.01)
*H04N 1/04* (2006.01)
*H04N 1/00* (2006.01)
*G06K 9/20* (2006.01)
*G06Q 50/24* (2012.01)
*G06K 9/00* (2006.01)
*G06Q 10/10* (2012.01)
*G16H 30/40* (2018.01)
*G16H 30/20* (2018.01)
*G16H 10/60* (2018.01)

(52) U.S. Cl.
CPC ....... *G06F 3/0482* (2013.01); *G06K 9/00449* (2013.01); *G06K 9/2081* (2013.01); *G06Q 10/10* (2013.01); *G06Q 50/24* (2013.01); *G16H 10/60* (2018.01); *G16H 30/20* (2018.01); *G16H 30/40* (2018.01); *H04N 1/00244* (2013.01); *H04N 1/00411* (2013.01); *H04N 1/04* (2013.01); *G06K 2209/01* (2013.01); *H04N 2201/0094* (2013.01)

(58) Field of Classification Search
CPC ..................................... G06F 3/0482
USPC ......................................... 715/810
See application file for complete search history.

(56) References Cited

U.S. PATENT DOCUMENTS 6,529,947 B1 * 3/2003 Feuerman ......... H04L 29/12141
709/203
7,406,599 B1 * 7/2008 Pravetz .............. G06K 9/00154
380/232

(Continued)

FOREIGN PATENT DOCUMENTS

JP 2003-067172 3/2003
JP 2003-150363 5/2003

(Continued)

OTHER PUBLICATIONS

Akimoto Yuya, JP Publication 2010074290, published Apr. 2, 2010 (Year: 2010).*

*Primary Examiner* — Reza Nabi
(74) *Attorney, Agent, or Firm* — Oblon, McClelland, Maier & Neustadt, L.L.P.

(57) ABSTRACT

An information processing apparatus includes circuitry to acquire an image of a document; extract a first part of the acquired image based on a first extraction region setting stored in a memory; and display a selection screen including the first part of the acquired image and a user list including one or more users. The first part of the acquired image allows a user to recognize a first user indicated by the first part of the acquired image, and the user list allows the user to select the first user.

10 Claims, 15 Drawing Sheets

(56) References Cited

U.S. PATENT DOCUMENTS

| | | | |
|---|---|---|---|
| 8,423,385 B2* | 4/2013 | Radoccia | G06Q 20/10 |
| | | | 705/2 |
| 2005/0233290 A1* | 10/2005 | Jackson | G09B 19/00 |
| | | | 434/262 |
| 2009/0128859 A1* | 5/2009 | Daos | H04N 1/32203 |
| | | | 358/3.28 |
| 2011/0085205 A1* | 4/2011 | Ouchi | G06F 3/1221 |
| | | | 358/1.15 |
| 2011/0279842 A1* | 11/2011 | Abe | H04N 1/00514 |
| | | | 358/1.13 |
| 2013/0031174 A1* | 1/2013 | Baba | G06F 9/5033 |
| | | | 709/204 |
| 2014/0201081 A1* | 7/2014 | Neuwirth | G06Q 20/3825 |
| | | | 705/44 |
| 2015/0039377 A1* | 2/2015 | Baba | G06Q 10/06315 |
| | | | 705/7.25 |
| 2015/0264184 A1* | 9/2015 | Baba | H04M 3/565 |
| | | | 370/261 |
| 2016/0274745 A1* | 9/2016 | Baba | G06F 3/0482 |
| 2017/0097747 A1* | 4/2017 | Allen | G06F 3/0482 |
| 2017/0098035 A1* | 4/2017 | Grevious | G16H 15/00 |

FOREIGN PATENT DOCUMENTS

| | | |
|---|---|---|
| JP | 2008-126588 | 6/2008 |
| JP | 2010-074290 | 4/2010 |
| JP | 2010-217983 | 9/2010 |
| JP | 2011-239088 | 11/2011 |
| JP | 2014-000785 | 1/2014 |

* cited by examiner

FIG. 7

| PATIENT ID | NAME OF PATIENT | STATUS OF PATIENT | NAME OF DOCTOR IN ATTENDANCE | .... |
|---|---|---|---|---|
| 1 | JIRO TANAKA | PREHOSPITAL | HIROAKI IKEDA | .... |
| 2 | HANAKO YAMADA | PREHOSPITAL | AKIO OHNO | .... |
| 3 | KAZUO SATOH | PREHOSPITAL | HIROSHI SASAKI | .... |
| 4 | JIRO ITOH | PREOPERATIVE | KOUJI YAMAGUCHI | .... |
| 5 | AKIKO MURAYAMA | PREOPERATIVE | JIRO TANAKA | .... |
| 6 | SABURO TAKAHASHI | BEFORE TRANSFUSION | YOSHIO FUJIMURA | .... |
| 7 | MASAO SAITO | PREHOSPITAL | HIROAKI IKEDA | .... |
| 8 | SINICHI SUZUKI | PREOPERATIVE | JIRO TANAKA | .... |
| 9 | NATSUKO ENDO | BEFORE TRANSFUSION | YOSHIO FUJIMURA | .... |
| .... | .... | .... | .... | .... |

FIG. 8

| DEVICE ID | HOST NAME | IP ADDRESS | NAME OF DOCTOR | .... |
|---|---|---|---|---|
| 1 | MFP01 | 10.1.1.1 | HIROAKI IKEDA | .... |
| 2 | PRINTER02 | 10.1.1.2 | AKIO OHNO | .... |
| 3 | MFP03 | 10.1.1.3 | HIROSHI SASAKI | .... |
| 4 | MFP04 | 10.1.1.4 | KOUJI YAMAGUCHI | .... |
| 5 | PRINTER05 | 10.1.1.5 | JIRO TANAKA | .... |
| 6 | MFP06 | 10.1.1.6 | YOSHIO FUJIMURA | .... |
| .... | .... | .... | .... | .... |

FIG. 9

EXTRACTION REGION SETTING SCREEN

DOCUMENT TYPE: ADMISSION AGREEMENT

NAME OF EXTRACTION REGION: PATIENT SIGNATURE

STATUS OF PATIENT: PREHOSPITAL ▽

DOCUMENT NAME REGION: (50, 45), (135, 50)

EXTRACTION REGION: (75, 200), (175, 250)

REGISTER

FIG. 10A

| DOCUMENT ID | DOCUMENT NAME (DOCUMENT TYPE) | DOCUMENT NAME REGION | EXTRACTION REGION NAME | EXTRACTION REGION | STATUS OF PATIENT | ... |
|---|---|---|---|---|---|---|
| 1 | ADMISSION AGREEMENT | (50, 45), (135, 50) | PATIENT SIGNATURE | (75, 200), (175, 250) | PREHOSPITAL | ... |
| 2 | SURGICAL CONSENT FORM | (50, 225), (150, 250) | PATIENT SIGNATURE | (100, 55), (180, 85) | PREOPERATIVE | ... |
| 3 | TRANSFUSION AGREEMENT | (50, 100), (150, 125) | PATIENT SIGNATURE | (50, 250), (100, 275) | BEFORE TRANSFUSION | ... |
| ... | ... | ... | ... | ... | ... | ... |

FIG. 10B

| PATIENT STATUS ID | STATUS OF PATIENT |
|---|---|
| 1 | PREHOSPITAL |
| 2 | PREOPERATIVE |
| 3 | BEFORE TRANSFUSION |
| ... | ... |

FIG. 13

EXTRACTION REGION SETTING SCREEN 201

801

DOCUMENT TYPE: ADMISSION AGREEMENT

NAME OF EXTRACTION REGION 1: PATIENT SIGNATURE

NAME OF EXTRACTION REGION 2: DOCTOR SIGNATURE

STATUS OF PATIENT: PREHOSPITAL ▽

DOCUMENT NAME REGION: (50, 45), (135, 50)

EXTRACTION REGION 1: (75, 200), (175, 250)

EXTRACTION REGION 2: (75, 250), (175, 300)

REGISTER 850
851
852

FIG. 14

| DOCUMENT ID | DOCUMENT NAME (DOCUMENT TYPE) | DOCUMENT NAME REGION | EXTRACTION REGION 1 NAME (ATTRIBUTE 1) | EXTRACTION REGION 1 | PATIENT STATUS FOR SEARCH | EXTRACTION REGION 2 NAME (ATTRIBUTE 2) | EXTRACTION REGION 2 | ... |
|---|---|---|---|---|---|---|---|---|
| 1 | ADMISSION AGREEMENT | (50, 45), (135, 50) | PATIENT SIGNATURE | (75, 200), (175, 250) | PREHOSPITAL | DOCTOR SIGNATURE | (75, 250), (175, 300) | ...... |
| ... | ...... | ...... | ...... | ...... | ...... | ...... | ...... | ...... |

FIG. 15

| DOCTOR ID | NAME OF DOCTOR | ········ |
|---|---|---|
| 1 | HIROAKI IKEDA | ········ |
| 2 | AKIO OHNO | ········ |
| 3 | HIROSHI SASAKI | ········ |
| 4 | KOUJI YAMAGUCHI | ········ |
| 5 | JIRO TANAKA | ········ |
| 6 | YOSHIO FUJIMURA | ········ |
| .... | .... | ········ |

FIG. 16

| PATIENT ID | DOCTOR ID | ········ |
|---|---|---|
| 1 | 1 | ········ |
| 2 | 2 | ········ |
| 3 | 3 | ········ |
| 7 | 1 | ········ |
| .... | .... | ········ |

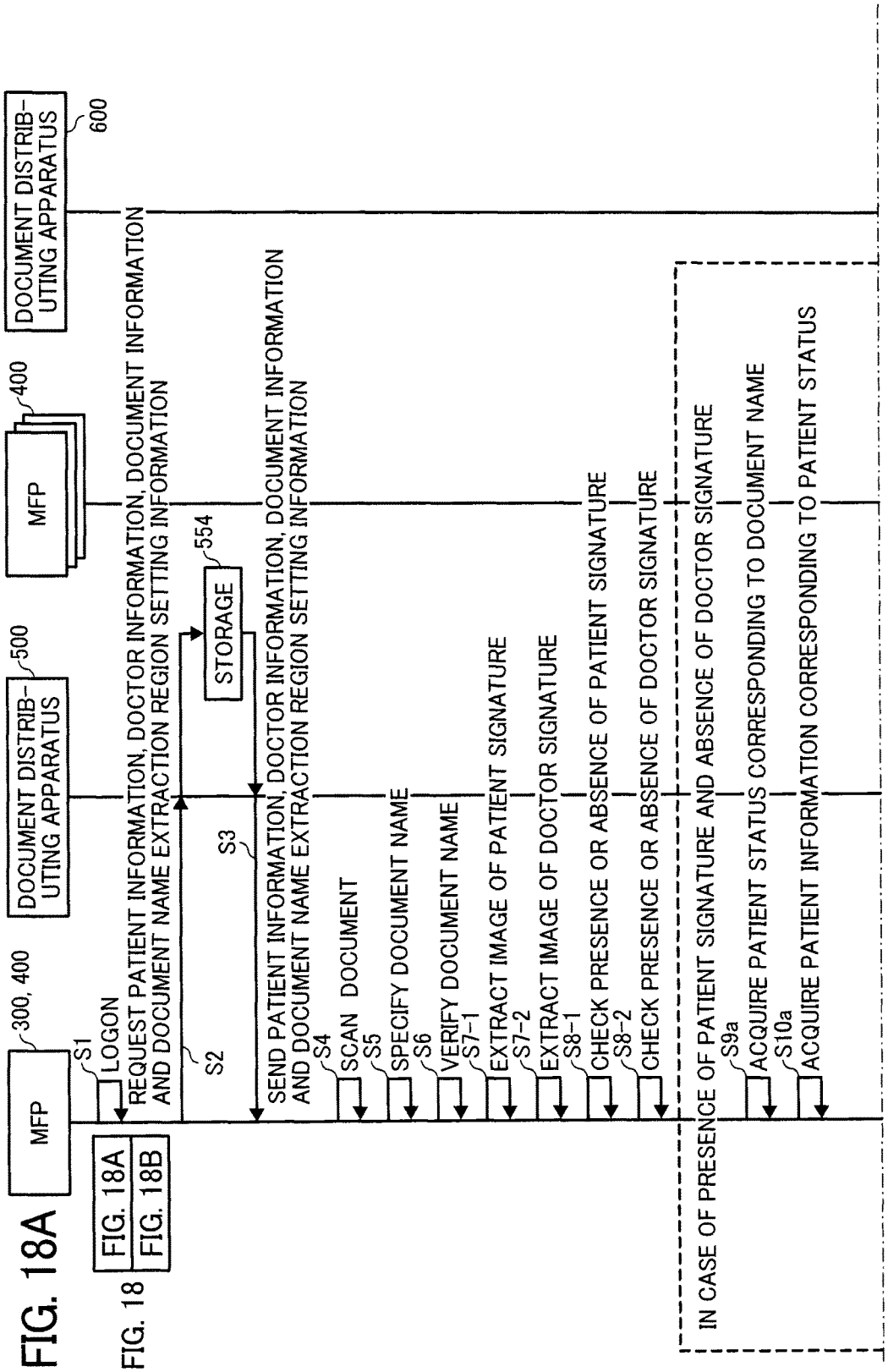

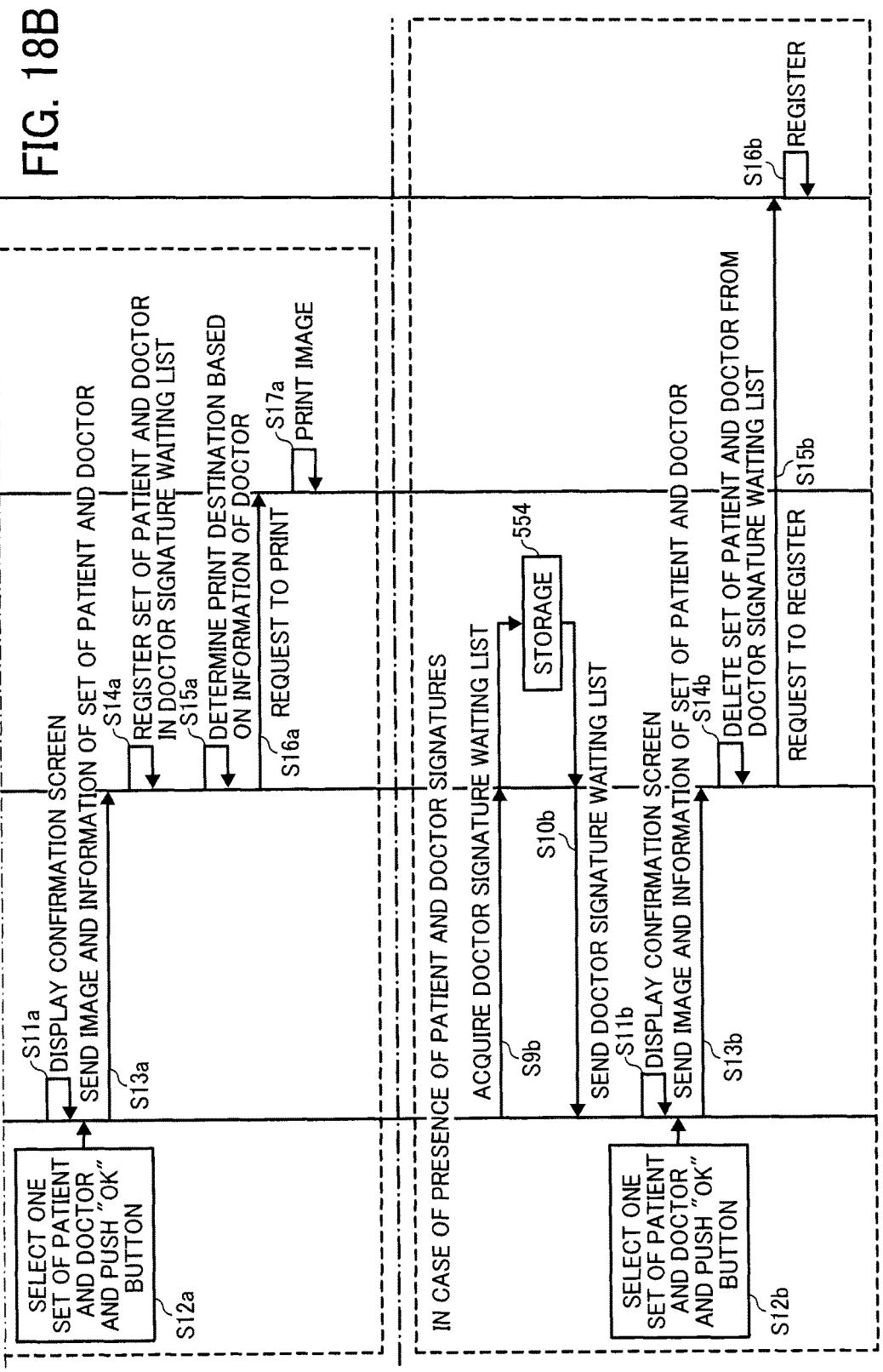

INFORMATION PROCESSING APPARATUS, INFORMATION PROCESSING SYSTEM, AND METHOD

CROSS-REFERENCE TO RELATED APPLICATION

The present application is based upon and claims the benefit of priority of Japanese Patent Application No. 2015-057765, filed on Mar. 20, 2015, the entire contents of which are incorporated herein by reference.

BACKGROUND

1. Field

One aspect of this disclosure relates to an information processing apparatus, an information processing system, and an information processing apparatus.

2. Description of the Related Art

Recently, there is a growing need for improvement of working efficiency with digitization of documents treated in the hospital. For example, it is known that an information processing system converts a document into electronic data by a scanning function implemented in a Multifunctional Peripheral (MFP) and manages the electronic data of the document on the personal computer (PC).

For example, there exists a solution technology for performing a workflow by distributing by e-mail or storing in a destination the text data scanned from a document.

Japanese Laid-open Patent Application No. 2010-074290 discloses an image forming apparatus recognizing content of a document, giving an authority automatically corresponding to the content and setting a destination of distribution corresponding to the content, when image data of the document is distributed for a purpose of execution of processing, corresponding to the content of the document to be digitized and output without user handling.

In particular, the image forming apparatus scanning the document, extracting a character string from scanned information, and executing a process corresponding to the extracted character string is disclosed.

However, in the past, it has been difficult to recognize a content written by a user on the document mechanically. For example, sometimes the content, such as a signature written by a patient's hand on paperwork treated in the hospital, is confirmed visually because the character string is not extracted from the content automatically. In this case, hospital staff, such as a receptionist, may check the content of the paperwork against verification information, such as information displayed on a screen of a personal computer (PC) or described in a patient registration card. This confirmation work is not convenient because the content for confirmation and the verification information are displayed in different ways (for example, on paper, on the PC's screen, or on the patient registration card).

Moreover, such a problem does not only occur with the document written by a human's hand, but also with a document including content that is hard to recognize automatically.

SUMMARY

In an exemplary implementation, there is provided an information processing apparatus, comprising circuitry configured to acquire an image of a document; extract a first part of the acquired image based on a first extraction region setting stored in a memory; and display a selection screen including the first part of the acquired image and a user list including one or more users, and wherein the first part of the acquired image allows a user to recognize a first user indicated by the first part of the acquired image, and the user list allows the user to select the first user.

In another exemplary implementation, there is provided an information processing system, comprising a memory to store a first extraction region setting; and circuitry configured to acquire an image of a document; extract a first part of the acquired image based on the first extraction region setting; and display a selection screen including the first part of the acquired image and a user list including one or more users, and wherein the first part of the acquired image allows a user to recognize a first user indicated by the first part of the acquired image, and the user list allows the user to select the first user.

BRIEF DESCRIPTION OF THE DRAWINGS

FIG. 7 illustrates a table of an exemplary configuration of patient information stored in the document distributing apparatus.

FIG. 8 illustrates a table of an exemplary configuration of device information stored in the document distributing apparatus.

FIG. 9 illustrates an exemplary configuration of an extraction region setting screen for setting document information at a client PC in a first embodiment.

FIG. 10A illustrates a table of an exemplary configuration of document information stored in the document distributing apparatus in a first embodiment.

FIG. 10B illustrates a table of an exemplary configuration of patient status information stored in the document distributing apparatus.

FIG. 13 illustrates an exemplary configuration of the extraction region setting screen for setting document information at a client PC in a second embodiment.

FIG. 14 illustrates a table of an exemplary configuration of the document information stored in the document distributing apparatus in the second embodiment.

FIG. 15 illustrates a table of an exemplary configuration of doctor information stored in the document distributing apparatus in the second embodiment.

FIG. 16 illustrates a table of an exemplary configuration of a doctor's waiting list stored in the document distributing apparatus in the second embodiment.

FIGS. 18A and 18B illustrate a sequence chart of an exemplary process performed by an information processing system in the second embodiment.

DETAILED DESCRIPTION

Figure 1:
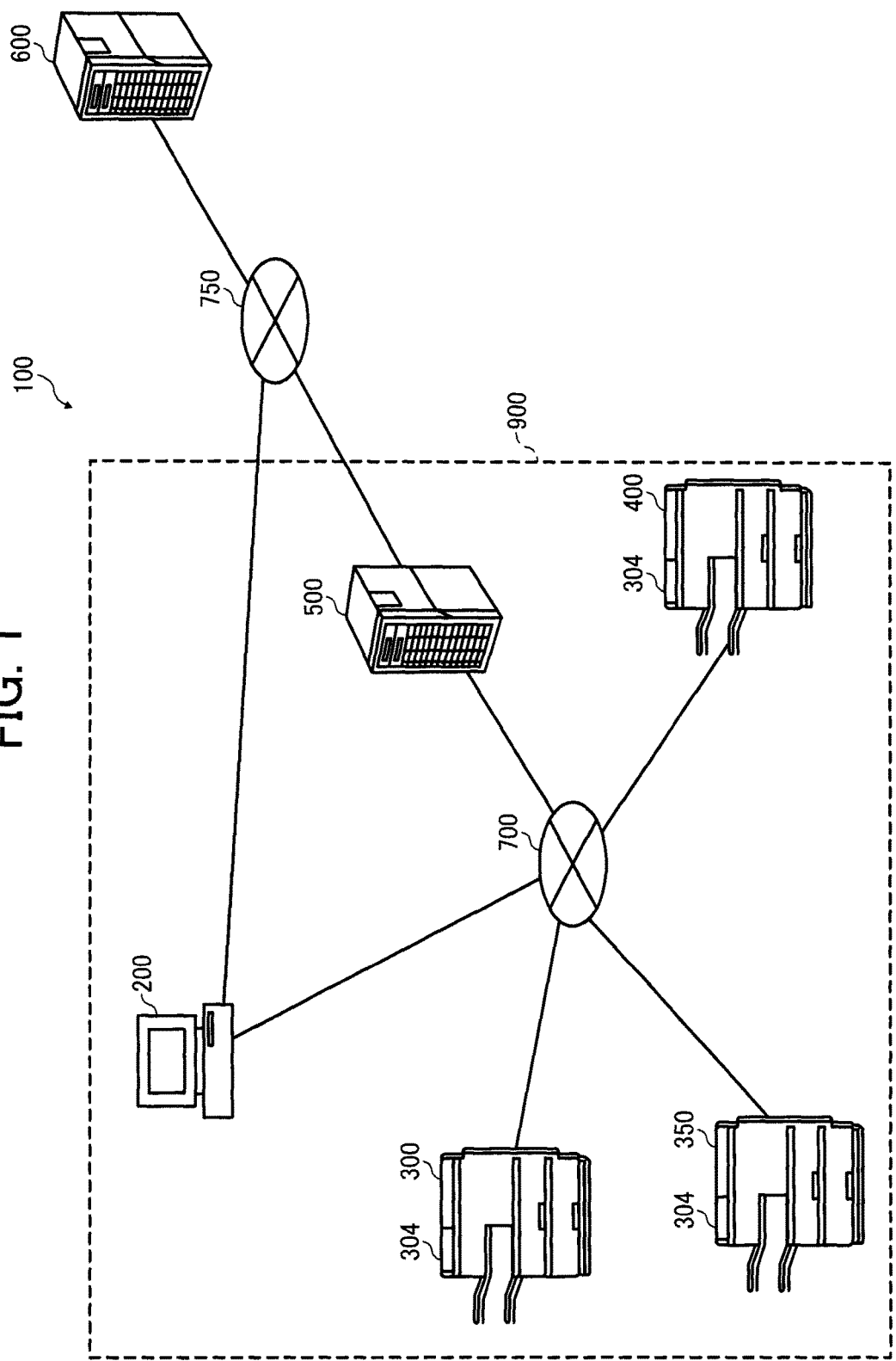
FIG. 1 illustrates an exemplary configuration of an information processing system.

The present disclosure is related to an information processing apparatus, an information processing system, a control method of the information processing system and a program. For example, at the information processing system in the hospital, a paper (document) on which a signature of a patient is written is processed for recognition and is sent to a primary doctor associated with the patient automatically, thus eliminating human error and reducing handling time by hospital staff.

One embodiment is explained in detail by referring to the drawings. Repeated use of reference characters in each drawing is intended to represent the same or analogous features or elements, and a repeated detailed description is omitted. One embodiment is described below. However, this disclosure is not limited the following embodiment. The following embodiment is explained with respect to a case where the information processing system is applied at a hospital, but this disclosure also may be applied anywhere that requires a similar information process.

FIG. 1 is a drawing illustrating an exemplary configuration of an information processing system 100.

As illustrated in FIG. 1, the information processing system 100 related to this embodiment may include an in-hospital information processing system 900, a document management apparatus 600 installed outside the hospital connected to each other via a network 750. The document management apparatus 600 is also connected with a client's personal computer (client PC) 200 via the network 750. The in-hospital information processing system 900 is connected with the client PC 200, multifunction peripherals (MFP) 300, 350, and 400, which are examples of an image forming apparatus, and a document distributing apparatus 500 via a network 700.

The document management apparatus 600 is set outside the hospital in FIG. 1. This assumes that the document management apparatus 600 is operated and managed by a company specializing in electronic health record systems of one or more hospitals. In this case, it is also assumed that the in-hospital information processing system 900 is provided by a specific company undertaking document management of the hospital, and being different from the company of the document management apparatus 600. Thus, the in-hospital information processing system 900 connects to the document management apparatus 600 via the network 750.

Moreover, in one embodiment, it may be assumed that one company operates and manages the document management apparatus 600 and provides the in-hospital information prcessing system 900. In this case, the document management apparatus 600 may be installed in the hospital. Alternatively, an apparatus integrated combination of a functon of the document management appratus 600 and a function of the document distributing apparatus 500 may be provided.

Furthermore, format data of a document consisting of a predetermined form used in the hospital, for example, an Admission Agreement for a hospital stay, may be stored in any one of the document management apparatus 600, the document distributing apparatus 500, and the client PC 200.

As described below, the MFPs 300 and 350 have a scanning function and a printing function. For example, the MFPs 300 and 350 print the format data of the document and read image data of the printed document having been filled out by a patient (user). The MFP 400 also has a scanning function and a printing function. For example, the MFP 400 is installed in an examination room of a doctor in attendance of the patient who prints the document having been filled out by the patient, such as an Admission Agreement, with a signature of the patient, and reads image data of the printed document having been filled out by the doctor.

The client PC 200 displays a user interface (hereafter referred to as a "UI") for operating the document distributing apparatus 500. The document distributing apparatus 500 stores information, as described below, such as a patient information table, a document information table, document name extraction region setting information, and a device information table. Further, the document distributing apparatus 500 executes a predefined process for the MFP 400 or the document management apparatus 600.

The network 700 may be a local area network laid in the hospital or an established private cloud network. The network 750 may be a public line network, such as the Internet, when the document management apparatus 600 is installed outside the hospital.

Figure 2:
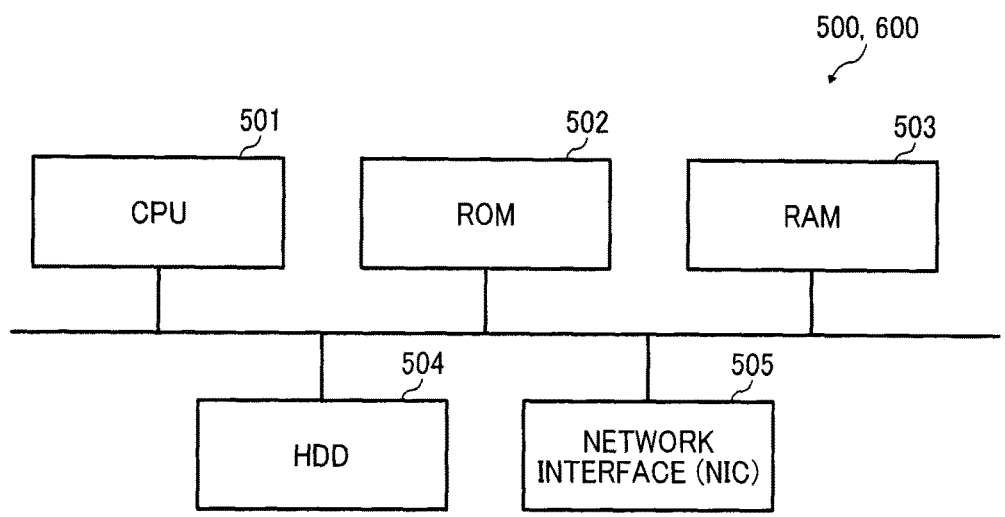
FIG. 2 illustrates an exemplary hardware configuration of a document distributing apparatus of the exemplary information processing system.

FIG. 2 is a block diagram illustrating an exemplary hardware configuration of the document distributing apparatus 500 according to one embodiment.

The document distributing apparatus 500 and the document management apparatus 600 has a similar configuration. As illustrated in FIG. 2, the document distributing apparatus 500 may include a Central Processing Unit (CPU) 501 controlling an overall operation in the document distributing apparatus 500, a read-only memory (ROM) 502 storing programs executed by the CPU 501, a random access memory (RAM) 503 storing data obtained by the CPU executing the programs temporarily, and a network interface (I/F) 505 being an interface to the network 700 or the network 750. The network I/F 505 may be a network interface card (NIC).

The document distributing apparatus 500 further includes a hard disk drive (HDD) 504. As described below, the HDD 504 stores information about a document form, an extraction region for the document, a name of the patient, a status of the patient, and a name of the doctor in attendance of the patient. Moreover, the HDD 504 stores an identifier for identifying the patient, an identifier for identifying the doctor, an identifier for identifying a device, such as the MFP, installed in the examination room of the doctor.

Figure 3:
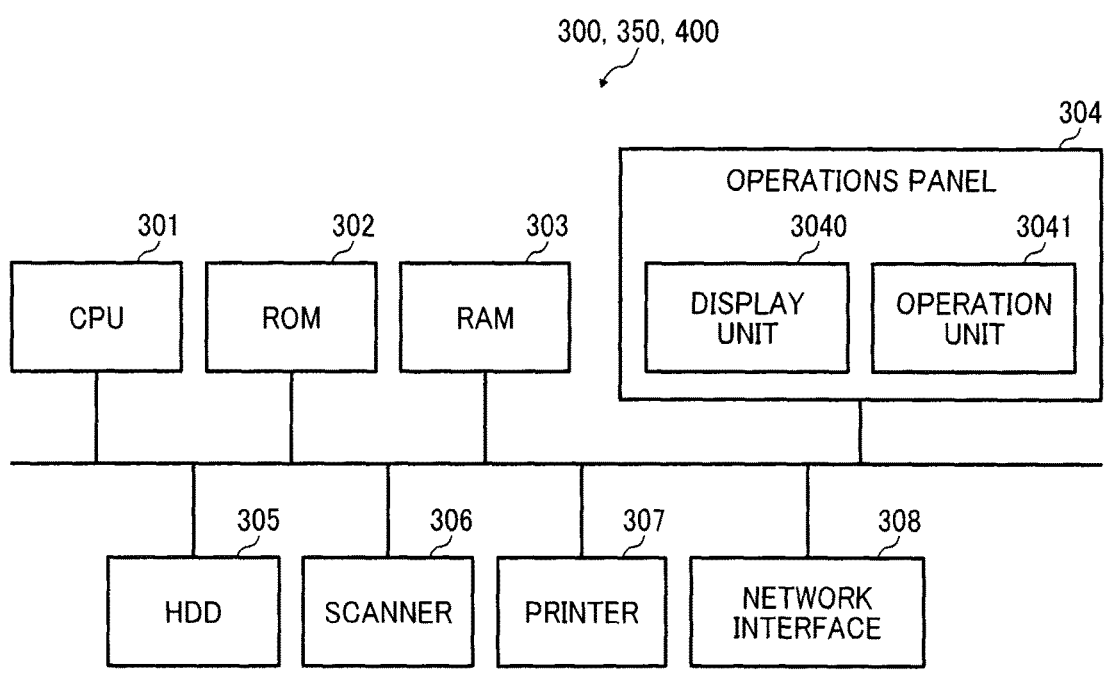
FIG. 3 illustrates an exemplary hardware configuration of a multifunction peripheral of the exemplary information processing system.

FIG. 3 is a block diagram illustrating an exemplary hardware configuration of the MFP 300 according to the one embodiment.

The MFPs 350 and 400 have the same hardware configuration of the MFP 350. As illustrated in FIG. 3, the MFP 300 may include CPU 301 controlling an overall operation of the MFP 300, a ROM 302 storing programs executed by the CPU 301, a RAM 303 storing data obtained by the CPU executing the programs temporarily, HDD 305 storing application programs to be executed, and a network I/F 308 to connect with the network 700 and communicate with the document distributing apparatus via the network 700.

Moreover, the MFP 300 may include a scanner 306 to scan a document, a printer 307 executing a print operation, an operations panel 304 accepting an operation by a user and including a display unit 3040 and an operation unit 3041. The display unit 3040 is constructed from a display such as a liquid crystal display (LCD). The operation unit 3041 is constructed from hardware keys such as buttons or software keys set on the display unit 3040, such as a touch-panel display.

Figure 4:
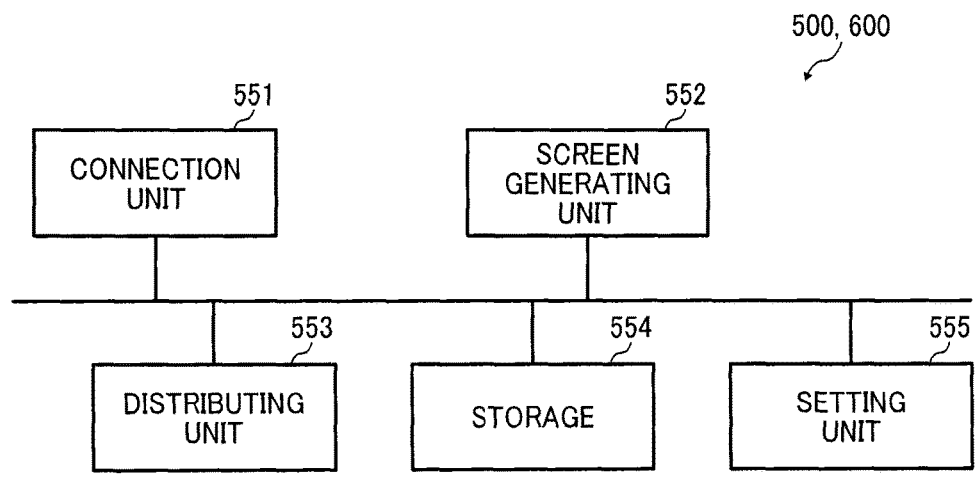
FIG. 4 illustrates an exemplary functional configuration of the document distributing apparatus of the exemplary information processing system.

FIG. 4 is a drawing illustrating an exemplary functional configuration of the document distributing apparatus 500 included in the information processing system 1 according to one embodiment.

The document distributing apparatus 500 may include a connection unit 551, which communicates with the MFPs 300, 350, and 400, the client PC 200, and the document management apparatus 600. The document distributing apparatus 500 may include a screen generating unit 552, which generates one or more screens for setting regarding process control for the document and recognition area of the document and provides the screen to the client PC 200 via the connection unit 551. The document distributing apparatus 500 may include a storage 554, which stores the patient information table, the document information table, document name extraction region setting information, and the device information table.

The document distributing apparatus 500 may include a setting unit 555, which sets information via the screen generated by the screen generating unit 552 and displayed on the client PC 200. The document distributing apparatus 500 may include a distributing unit 553, which instructs the MFP installed in the examination room of the doctor in attendance of the patient to output (print) the document, and sends the image data of the scanned document to the document management apparatus 600.

Figure 5:
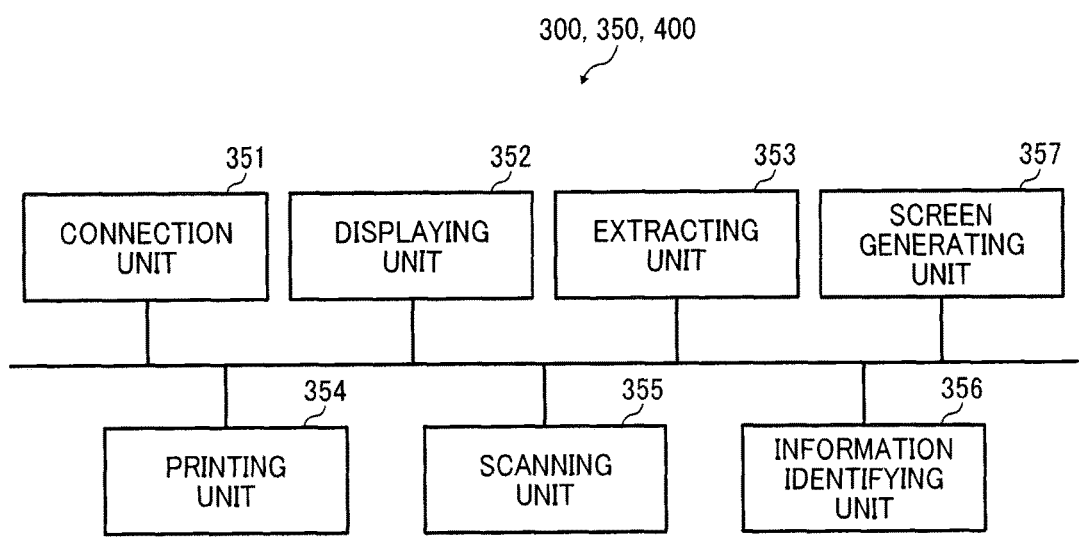
FIG. 5 illustrates an exemplary functional configuration of the multifunction peripheral of the exemplary information processing system.

FIG. 5 is a drawing illustrating an exemplary functional configuration of the MFP 300 included in the information processing system 1 according to one embodiment.

The MFPs 300, 350, and 400 have almost the same configuration. The MFP 300 may include a connection unit 351 that communicates with the document distributing apparatus 500. The MFP 300 may include a displaying unit 352, which generates a notification screen indicating that there is an error and displays the notification screen on the operations panel 304. The MFP 300 may include a scanning unit 355, which executes reading of the document and a printing unit 354, which executes printing of the document read or sent.

The MFP 300 may include an extracting unit 353 that extracts image data within a predetermined region from the image data of the document read by the scanning unit 355. The MFP 300 may include an information identifying unit 356, which executes optical pattern matching processing using, e.g., an Optical Character Reader (OCR), against the image data in the predetermined region extracted by the extracting unit 353, and acquires a character recognized by the optical pattern matching processing. The MFP 300 may include a screen generating unit 357, which generates a screen shown in FIG. 11 and FIG. 17, and control the display of the generated screen.

Figure 6A:
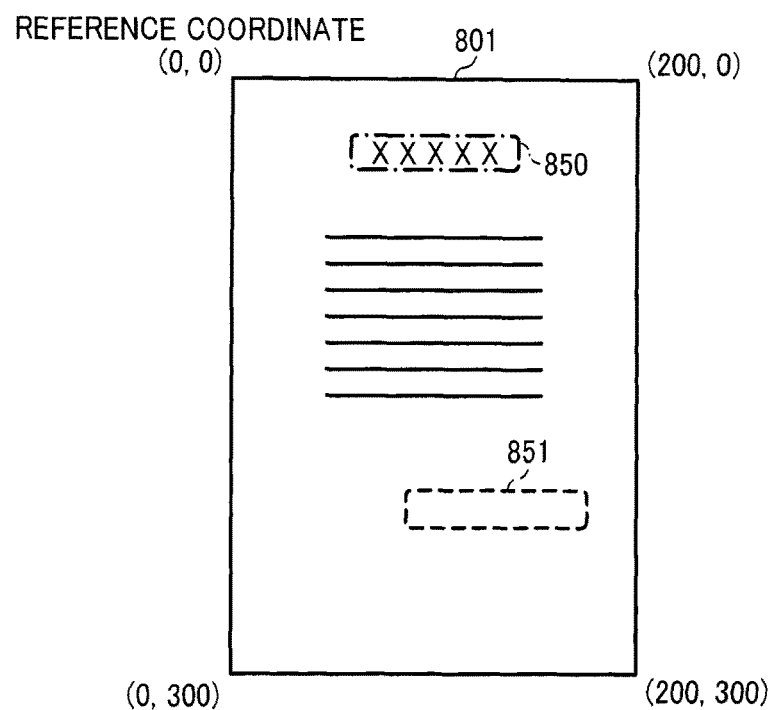
FIG. 6A illustrates an exemplary configuration of a format of a document.
Figure 6B:
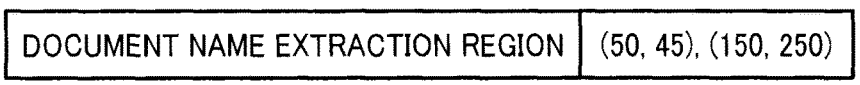
FIG. 6B illustrates a table of an exemplary configuration of a document name extraction region setting information.
Figure 6C:
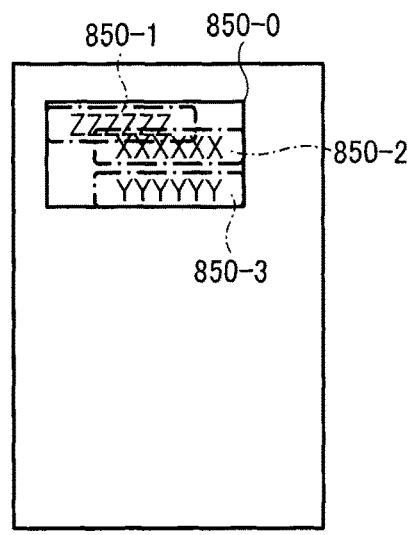
FIG. 6C illustrates an exemplary configuration of the document name extraction regions, each corresponding to a plurality of the documents.

Next, coordinates of the document, a document name extraction region setting information, and an area including the region of the document name of all documents used in the hospital, which are used for reading the document at the MFP 300 in the information processing system 1 according to one embodiment, are explained. FIG. 6A is a drawing illustrating coordinates, a name, and a signature block of the document. FIG. 6B is a drawing illustrating a document name extraction region setting information. FIG. 6C is a drawing illustrating an area including the region of the document name of all documents used in the hospital.

Document 801 in FIG. 6A indicates an Admission Agreement as one example. When the scanning unit 355 of the MFP 300 reads a document name 850 and a signature block 851 of the Admission Agreement 801, coordinate values are used. For example, the coordinate values of an upper left of the document 801 are defined as (0,0) which are reference coordinates, an upper right is (200,0), a lower left is (0,300) and a lower right is (200,300). Based on the coordinates of these four corners, the extracting unit 353 extracts the document name 850 of the Admission Agreement 801. There are several methods for extracting the document name 850 of the Admission Agreement 801.

<Method 1>

A user sets a document name or a document type of the document to be scanned via a predetermined screen displayed on the operations panel 304 before Or after scanning the document. After that, the document name set by the user is checked. In particular, the extracting unit 353 acquires the document name extraction region setting information corresponding to the document name set by the user from the document information table shown below in FIG. 10A, and extracts image data in a region from the scanned image of the document based on the coordinate values of the document name extraction region setting information (50,45) and (150, 250).

Then, the information identifying unit 356 executes the OCR processing on the extracted image data and acquires recognized character information. The extracting unit 353 checks whether the acquired character information and the document name set by the user match. When the acquired character information and the document name set by the user do not match, the extracting unit 353 determines that the set document name is not appropriate, and the displaying unit 352 displays a notification screen indicating that the set document name is not correct. When the acquired character information and the document name set by the user match, the extracting unit 353 determines that the set document name is correct. In method 1, the user has to set the document name each time manually. A method 2 explained below reduces the time and effort for setting the document name because the user need not set the document name each time. It should be noted that the step of checking whether the acquired character information and the set document name match can be omitted.

<Method 2>

A document name extraction region of the document name extraction region setting information in FIG. 6B is set at the document distributing apparatus 500 beforehand. The document name extraction region 850-0, such as shown in the FIG. 6C, indicates one or more regions, for example 850-1, 850-2, and 850-3 in FIG. 6C, which cover document name regions of all formed documents treated in the hospital.

Then, when the document is scanned, the extracting unit 353 acquires the document name extraction region from the document name extraction region setting information, shown in FIG. 6B, and extracts image data in the one or more regions indicated by coordinate values of the document name extraction region. The information identifying unit 356 executes the OCR processing on the extracted image data and acquires the recognized character information. The extracting unit 353 searches the document name including the recognized character information from all of the document names registered in the document information table shown in FIG. 10A. If there is no document name obtained by the searching, the displaying unit 352 displays a notification screen to notify a search result to the user. When at least one of the document name is obtained, the extracting unit 353 identifies the obtained document name as the document name of the document 801.

Thus, the identified document name in method 2 is the same as the set document name in method 1. The user need not set the document name each time, and the time and effort for setting the document name is reduced in method 2. This embodiment is explained based on method 2 as one example.

Next, patient information stored in a patient table in the information processing system 1 according to one embodiment is explained. FIG. 7 is a table illustrating one example of the patient information in the information processing system 1 according to one embodiment.

A name of a patient is stored in an item of a name of a patient in the table. A status of the patient corresponds to the name of a patient, for each patient. The operations panel 304 of the MFP 300 shown in FIG. 11, described below, displays a screen including a patient whose status is "prehospital." So Jiro Tanaka, Hanako Yamada, Kazuo Sato, and Masao Saitoh are searched and displayed on the screen in FIG. 11 based on the patient information in the FIG. 7. Additionally, a name of a doctor in attendance of the patient is associated with each patient.

The patient information in the patient information table in the document management apparatus 600 shown in FIG. 7 is registered, changed, and deleted by use of the client PC 200. The document distributing apparatus 500 stores the patient information stored in the document management apparatus 600. For example, the document distributing apparatus 500 is synchronized with the document management apparatus 600, and when the client PC 200 registers, changes, or deletes the patient information, the document distributing apparatus 500 and the document management apparatus 600 update the patient information for keeping a coincidence of the patient information in the document distributing apparatus 500 and the document management apparatus 600.

Also, when the document management apparatus 600 stores patient information of another hospital, an item of information for identifying the hospital, such as a name of the hospital or a hospital ID (identifier), is added in the patient information table shown in FIG. 7 for managing patient information of each hospital. Further, the patient information of one of the hospitals may be synchronized only between the document distributing apparatus 500 of one of the hospitals and the document management apparatus 600, based on the name of the hospital or the hospital ID.

FIG. 8 is a table illustrating device information stored in the device information table in the information processing system 1 according to one embodiment.

The device information table associates a name of a doctor, a host name of a device located in an examination room of the doctor, such as a MFP or a printer, and a destination of the device on the network, such as an Internet protocol (IP) address of the device. The device information table is stored in the storage 554 of the document distributing apparatus 500 beforehand.

The document distributing apparatus 500 selects (explained later with respect to FIG. 9 and FIG. 10A), the IP address associated with the host name of the device located in the examination room of the doctor in attendance of the patient whose signature is written in the document read by the MFP 300 or another device. Then the document distributing apparatus 500 requests the host of the selected IP address to output the document that is filled in with a patient signature.

It should be noted that the device information stored in the device information table shown in the FIG. 8 may include at least one type of information, for example, the IP address or the host name, identifying the device uniquely on the network. Also, the device ID may or may not be stored in the device information table. For example, the scanned image of the document is sent to the device based on the IP address of the device corresponding to the name of doctor, and the device outputs the scanned image.

Then, in the information processing system 1 according to one embodiment, one example of a screen displayed at the client PC 200 for setting information of the document information table before scanning the document at the MFP 300 is explained. Also, one example of the document information stored in the document information table and of the status of a patient stored in the patient information table are explained.

FIG. 9 is a drawing illustrating a screen displayed at the client PC 200 for setting information of the document information table before scanning the document at the MFP 300 in the information processing system 1 according to one embodiment. Also, FIG. 10A is a table illustrating document information stored in the document information table, and FIG. 10B is a table illustrating a status of a patient (user status) stored in the patient information table.

As described above, the in-hospital information processing system 900 is often a system provided by a specific company undertaking document management in the hospital. Thus, a user working for the specific company may set, to the MFP 300, an extracting process performed by the extracting unit 353 of the MFP 300.

The user accesses the document distributing apparatus 500 by the client PC 200 and sets information via a setting screen 201. For example, when the format document 801 is an Admission Agreement, the user designates an extraction region in the Admission Agreement by a pointing device, such as a mouse. In the case of FIG. 9, the extraction region of the name of document 850 in the Admission Agreement is designated, and "Admission Agreement" is input in an entry field of the document type on an upper right screen by the user. Next, the extraction region of the signature of the patient 851 in the Admission Agreement is designated and "patient signature" is input in an entry field of the name of extraction region under the entry field of the document type. In this way, a patient signature written in the extraction region 851 can be extracted when the name of the document extracted from the extraction region 850 is the document type "Admission Agreement".

Further, the user selects a status of the patient to be associated with the document type "Admission Agreement". As shown in FIG. 7, the status of patient to be stored in the patient information table is able to be displayed on the setting screen 201 and selected by the user. In the case of the Admission Agreement, the status of the patient "prehospital" is selected from a pull-down menu of the status of the patient, because the patient is not hospitalized yet before the patient signs the Admission Agreement. The information set via the setting screen 201 is stored in the storage 554 of the document distributing apparatus 500. Also, the status of the patient indicating that consent of the patient is needed, such as "prehospital," "preoperative," and "before transfusion," may be stored in the patient status table shown in the FIG.

10B. In this case, the patient information stored in the patient status table is displayed as a choice of an item of the status of patient. The patient status table may be acquired from the document distributing apparatus 500.

As shown in FIG. 10A, the storage 554 of the document distributing apparatus 500 stores the information set for three types of documents "Admission Agreement", "Surgical Consent Form" and "Transfusion Agreement". Further, a region having a document name corresponding to each document type is defined by coordinate values as a document name region, which is an example of first region information. Also, a region having a signature corresponding to each document type is defined by coordinate values as an extraction region. Supplementally, the coordinate values in FIG. 10A indicate the position of the diagonal. Thus, the storage 554 of the document distributing apparatus 500 stores associated information including the document type, the document name region, and the extraction region in association with each other.

When the document type is the Admission Agreement, the document name is read in the region indicated by coordinate values (50,45) and (135,50), and the patient signature is read in the region indicated by coordinate values (75,200) and (175,250). When the document type is the Surgical Consent Form, the document name is read in the region indicated by coordinate values (50,225) and (150,250), and the patient signature is read in the region indicated by coordinate values (100,55) and (180,85). When the document type is the Transfusion Agreement, the document name is read in the region indicated by coordinate values (50,100) and (150,125), and the patient signature is read in the region indicated by coordinate values (50,250) and (100,275). As is apparent, an entry field of the document name and an entry field in which the patient signs are in one-to-one correspondence.

FIG. 10A shows one example in which the position of the document name and the patient signature on the document is different for each of the document types. However, it may occur in a hospital that the document name of the document including an entry field for a patient signature is read in a same region for all document types. In such a case, the coordinate values of the document name can be the same for all the document types. Similarly, when a region of an entry field in which the patient signs is the same for all the document types, the coordinate values of the patient signature can be the same for all the document types.

A user, such as a system administrator of the hospital, sets information related to the document in the hospital by the client PC 200. The setting information input via the setting screen 201 is sent from the client PC 200 to the document distributing apparatus 500 and registered in the document information table. Similar to the patient information explained above and shown in FIG. 7, the document information may be stored in both the document management apparatus 600 and the document distributing apparatus 500, or in only the document distributing apparatus 500.

In particular, the "Admission Agreement" set in the item of the document type on the setting screen 201 is stored as "document name (document type)" in the document information table, a patient signature set in the item of the name of the extraction region on the setting screen 201 is stored as "extraction region name" in the document information table, and "prehospital" set in the item of the status of the patient on the setting screen 201 is stored as "status of patient" in the document information table. Regarding the status of a patient, for example, at least one status of patients to be registered in the patient information table shown in the FIG. 7 may be displayed by a drop-down list, and the user selects from the list.

Next, the coordinate values of the document name region (50, 45) and (135, 50), which the user selects by the mouse or by touching the displayed screen, are stored in the document name region of the document information table in FIG. 10A. The coordinate values of the extraction region (75, 200) and (175, 250), which the user selects by the mouse or by touching the displayed screen, are stored in the extraction region of the document information table in FIG. 10A. The user may set the coordinate values of the document name region and the extraction region by inputting the coordinate values directly without the mouse. When the user inputs the coordinate values, a currently set region corresponding to current input coordinate values may be displayed in the settng screen 201.

Also, the document ID is information identifying each document name (document type) uniquely and is given a new document name in registering. However, the document ID may not be needed when the document name can be the document ID. Further, the document management apparatus 600 handles the electronic health record system in the hospital, therefore the document management apparatus 600 stores a status of all patients (patient information of all patients) in the hospital and sends the patient information requiring consent, such as "prehospital," "preoperative," and "before transfusion," to the document distributing apparatus 500 to be stored in the storage 554. As will be described below, the document distributing apparatus 500 may acquire the patient information from the document management apparatus 600 when the user logs into the MFP 300.

Figure 11:
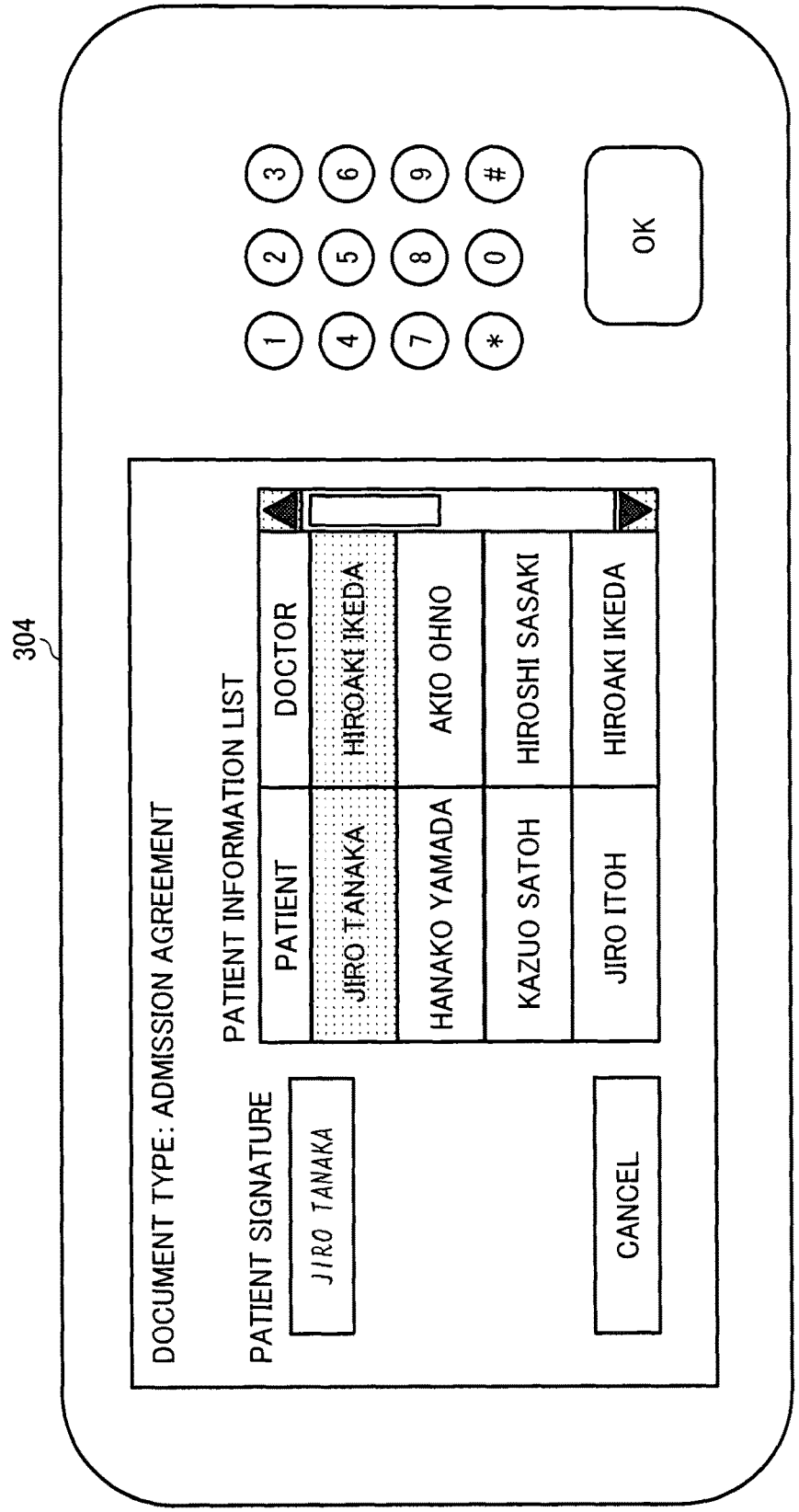
FIG. 11 illustrates an exemplary configuration of a confirmation screen at the multifunction peripheral in the first embodiment.

FIG. 11 is a drawing illustrating a screen displayed at the operations panel at the MFP 300 in the information processing system 1 according to one embodiment.

The user, for example, a staff person in the hospital, uses the MFP 300 to read the document of the Admission Agreement including the signature of the patient Jiro Yamada by the scanning unit 335. Then, the MFP 300 reads the document and displays a screen specifying the Admission Agreement as the document type in the operations panel shown in FIG. 11. Also, the image of the signature by Jiro Yamada, which is an image extracted based on the coordinate values of the extraction region, is displayed as the patient signature on the screen. Thus, the displayed image on the operations panel includes contents filled in by the patient.

Further, the patient information list displayed on the screen, which is one example of a user list, includes a name of patient and a name of the doctor in attendance of the patient based on the patient information. The status of every patient included in the patient information list matches the status of a patient corresponding to the Admission Agreement by searching in the patient information table. A user instructing the MFP 300 to read the Admission Agreement confirms the name of the patient based on the patient signature displayed on an upper left side of the screen, and selects a set of the patient and the doctor including the confirmed patient from among the patient information list displayed on right side of the screen. Then, the user presses an "OK" button. If the user could not find out the appropriate patient from the patient information list, he presses a "cancel" button. It should be noted that this operation is executed by the doctor or nurse usually, not by the staff person in the hospital. Also, it is not required that the displayed screen include the name of the doctor in attendance of the patient. In this case, the user selects the appropriate patient included in the patient list. On the other hand, it is insufficient for the name of the patient only to specify the patient related to the Admission Agreement. For example, if two patients have the same name, an examination subject of the patient may be displayed on the screen in association with the patient.

<Operation of First Embodiment>

Figure 12:
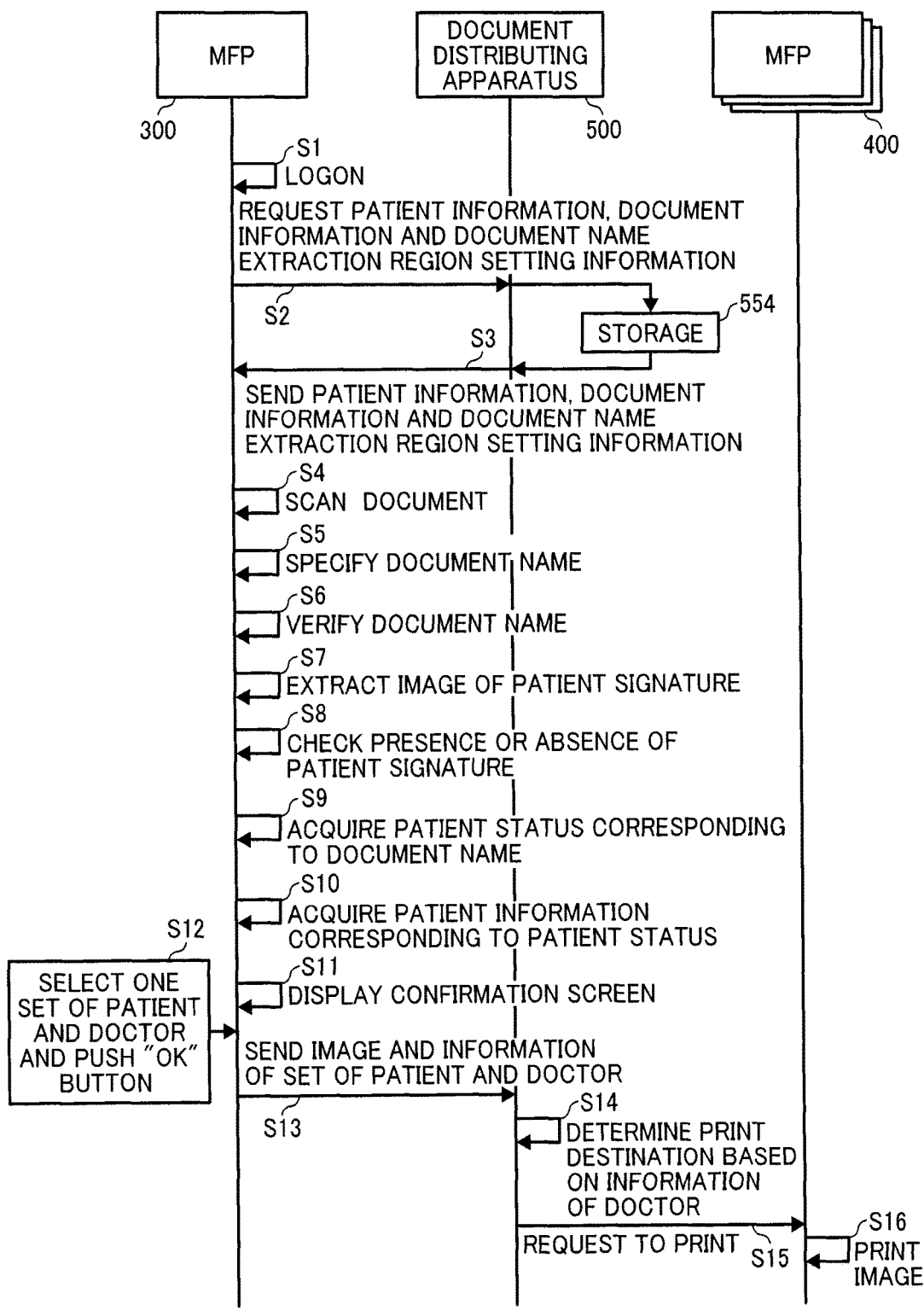
FIG. 12 illustrates a sequence chart of an exemplary process performed by an information processing system in the first embodiment.

Next, an operation of a first embodiment in the information processing system 1 will be described. FIG. 12 shows one example of a sequence about the operation in the first embodiment.

At first, a user, such as a staff person in the hospital, accesses and logs on to the MFP 300 (Step S1). The logging on to the MFP 300 is executed by inputting a user name and password via a login screen on the operations panel 304 or holding up an IC card to a card reader. When the logon process succeeds, a lock status of the operations panel 304 is released, and the operations panel 304 displays a screen including a list of applications installed in the MFP 300 or a list of one or more workflows. This logon process is not required when the user can operate the MFP 300 without logging on.

Then, the MFP 300 accesses the document distributing apparatus 500 via the network 700 and requests acquisition of information in the storage 554 to the document distributing apparatus 500 (Step 2). The user selects one of the workflows of which name is a patient signature matching among the workflow list screen on the operations panel 304. Then, the MFP 300 acquires document name extraction region setting information, a patient information table, and a document information table from the storage 554 of the document distributing apparatus. As described above, the document name extraction region setting information in FIG. 6B, the patient information table in FIG. 7, and the document information table in FIG. 10A are preset by the extraction region setting screen and stored in the storage 554.

That is, the connection unit 351 requests, to the document distributing apparatus, acquisition of information stored in the patient information table, the document information table, and the document name extraction region setting information. All of that information may be required, or information needed only to perform a process may be required. For example, the document name extraction region setting information is acquired at step 5s, as described below.

The connection unit 551 responds to the patient information table, the document information table, and the document name extraction region setting information to the MFP 300 in response to the acquisition request.

The user operates the MFP 300 to read the document received from a patient (Step S4). The scanning unit 355 scans the document and generates image data of the document. Then, the document name of the scanned image data is extracted and specified by the extracting unit 353 and the information identifying unit 356 (Step S5). The extracting unit 353 and the information identifying unit 356 in the MFP 300 determines that the specified document type is correct or not (Step S6). If the document type (document name) is not specified in step S5, or the specified document type does not match the document type set by the user, the displaying unit 352 displays a screen to notify the user that an error has occurred. It should be noted that the determination process in step S6 may not be executed.

Then the extracting unit 353 extracts image data of a patient signature (Step S7). In particular, the extracting unit 353 acquires an extraction region corresponding to the specified document name and extracts image data corresponding to the coordinate values of the acquired extraction region from the scanned image data.

In step S8, the extracting unit 353 determines whether there is a patient signature or not based on the image data corresponding to the acquired extraction region. For example, the extracting unit 353 determines whether there is the patient signature based on an entry amount in the acquired extraction region. The entry amount is based on a ratio of a background color to other colors in the image data of the patient's signature. The extracting unit 353 determines that there is a patient signature when the ratio of the background color to other colors is more than a predetermined threshold. When the extracting unit 353 determines that there is no patient signature, the displaying unit 352 displays a screen to notify that an error has occurred.

When the extracting unit 353 determines that there is a patient signature, the MFP 300 request the document distributing apparatus 500 to search a status of the patient corresponding to the specified document type from the document information table in the storage 554 (Step S9). For example, the searched status of the patient is "prehospital" when the specified document type is Admission Agreement.

The extracting unit 353 acquires patient information in which the status of the patient is the searched status of the patient from the patient information table (Step S10). When any patient information is not acquired by the process in step S10, the displaying unit 352 displays the screen to notify that there is no selectable patient based on the document.

When patient information is acquired in step S10, the screen generating unit 357 generates a selection screen, and the displaying unit 352 displays the selection screen on the operations panel 304 (Step S11). The selection screen, as shown in FIG. 11, includes the specified document type, the extraction region name related to the specified document type, the extracted image data of the patient signature, and a list of one or more sets of names of the patient and a name of the doctor in attendance in the acquired patient information. The user at the MFP 300 can select one of the sets from the list via the selection screen.

The user at the MFP recognizes the patient based on the displayed image of the patient signature, selects one of the sets of patient and doctor names, including a name of the recognized patient and, then pushes an "OK" button via the selection screen (Step S12). When the user cannot recognize any patient from the displayed image of the patient's signature, he pushes a "Cancel" button.

The connection unit 351 of the MFP 300 sends the scanned image data of the document, the extracted image of the patient's signature, and the selected set of patient and doctor names to the document distributing apparatus 500 (Step S13).

The distributing unit 553 of the document distributing apparatus 500 determines an IP address of an output destination indicating an MFP located in the examination room of the doctor whose name is the doctor name in the selected set (Step S14). At step S14, the distributing unit 553 acquires the IP address corresponding to the selected doctor name from the device information table and determines that the acquired IP address is the output destination of the scanned image.

The connection unit 551 of the document distributing apparatus 500 sends a request of printing the scanned image of the document to a host of the determined IP address via the network 700 (Step S15). The host of the determined IP address indicates an output apparatus determined as the output destination. When the MFP 400 is designated as the output apparatus by the document distributing apparatus 500, the printing unit 354 of the MFP 400 executes to print the scanned document in response to the request (Step S16).

It should be noted that the process of step S13 may not be executed and the processes of steps S14 and S15 may be executed by the MFP 300 when the device information is acquired from the document distributing apparatus 500 in the processes of step S2 and S3. In this case, an output request is sent to the output destination without going through the document distributing apparatus 500.

The present embodiment shows that the document name extraction region setting information, the patient information, and the document information stored in the storage 554 in the document distributing apparatus 500 are acquired at steps S2 and S3. However the request of acquiring the status of a patient may be sent to the distributing apparatus 500 just before the step S10 because the status of a patient may fluctuate in real time more than the document information or the name of the patient.

The present embodiment also shows that the MFP 300 executes the processes from step S1 to step S12. However at least one of these processes may be executed by the document distributing apparatus 500. As described above, the document distributing apparatus 500 is able to implement functional units comprising the same functions as the displaying unit 352, the extracting unit 353, the screen generating unit 354, and the information identifying unit 356. Therefore, the processes from step S5 to step S12 may be executed by the document distributing apparatus 500.

<Modification of the First Embodiment>

The above first embodiment shows that the patient information list including patients matching the status of a patient corresponding to the document name are displayed on the confirmation screen, such as in FIG. 11, and the patient recognized based on the patient signature is selected from the list. Thus, the patients included in the list are specified based on the document name and patient status.

On the other hand, the document requesting the patient signature may include the name of the doctor in attendance. This name is not handwritten, but is printed. Therefore, the patients in the list can be specified based on the document name and the name of doctor in attendance.

In detail, an item of the doctor's name is added to the document information table shown in the FIG. 10A, and a doctor name region is set via the setting screen 201. A method of setting the doctor's name region is similar to the method of setting the document name region or the extraction region.

When the document is scanned, as described above, the document name is specified. The extracting unit 353 extracts image data of the doctor's name region corresponding to the specified document name. Then, the information identifying unit 356 acquires character information from the extracted image data, and the extracting unit 353 searches the doctor name matching the acquired character information from the patient information table. When the doctor's name is searched, the extracting unit 353 specifies all patients corresponding to the searched doctor's name from the patient information table, and the list, including all patients, is displayed on the confirmation screen, such as in FIG. 11.

The processing here is similar to that in the first embodiment. However, the patients included in the list may be specified based on the document name, the status of the patient, and the doctor's name. This makes the choices of selected target patients more narrow.

<Operation of a Second Embodiment>

Next, an operation of a second embodiment in the information processing system 1 is explained. FIG. 13 shows one example of a screen displayed on the client PC 200 when the MFP 300 scans the document.

The difference between FIG. 13 and FIG. 9 is that an entry field 852 for a doctor's signature is added. The right side of the setting screen 201 displays an input item of a name of a second extraction region and coordinate values of the second extraction region. In this case, the name of second extraction region is a doctor's signature, and the second extraction region corresponds to the entry field 852.

FIG. 14 is a table illustrating one example of document information according to the information processing system of the second embodiment. The difference between FIG. 14 and FIG. 10A is that an item of the extraction region 2 name and an item for the coordinate values of the second extraction region are added. The extraction region 1 in FIG. 14 corresponds to the extraction region in FIG. 10A, which is a first extraction region in the second embodiment, and the extraction region 2 in FIG. 14 corresponds to the second extraction region.

FIG. 15 is a table illustrating one example of doctor information stored in a doctor information table according to the information processing system of the second embodiment. FIG. 16 is a table illustrating one example of a doctor's waiting list according to the information processing system of the second embodiment.

Figure 17:
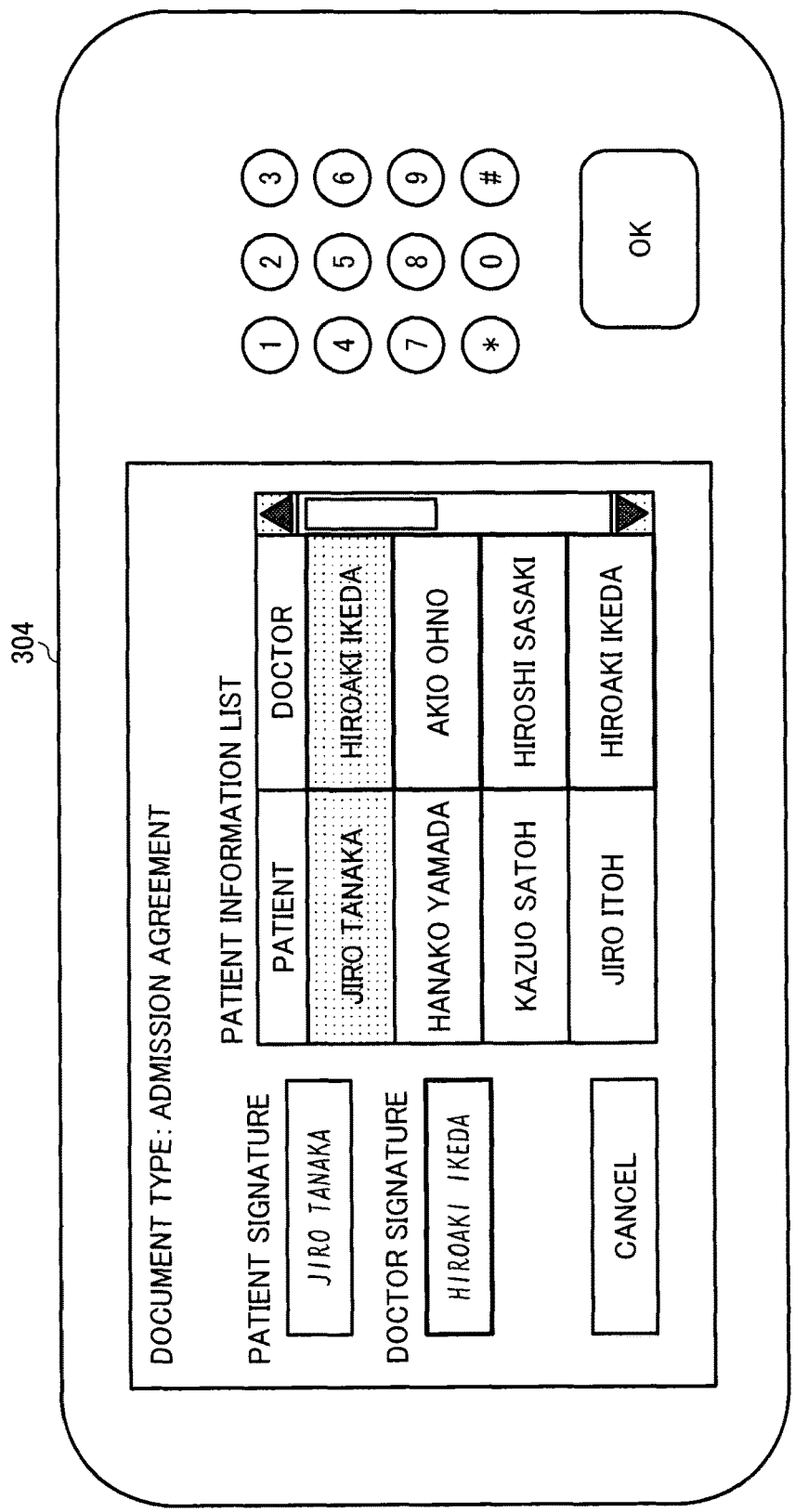
FIG. 17 illustrates an exemplary configuration of the confirmation screen at the multifunction peripheral in the second embodiment.

FIG. 17 shows one example of a screen displayed on the MFP 300 according to the information processing system of the second embodiment. The difference between FIG. 17 and FIG. 11 is that an image of the doctor signature written to the document by the doctor is added. It should be noted that all patients included in the list of patient information are selected from the doctor waiting list instead of the patient information.

In the second embodiment, it is explained how to register the scanned imaged data in the document management apparatus 600. In the present embodiment, the document is registered in the document management apparatus 600 after confirming that both the patient signature and the doctor signature are filled in within the document. The distributing unit 553 of the document distributing apparatus 500 according to the present embodiment controls an output destination based on the presence or absence of the patient signature and the doctor signature. FIGS. 18A and 18B show one example of a sequence of the operation in the second embodiment.

A user logs in to the MFP 300 in step S1 in the same way as in the first embodiment explained with respect to FIG. 12. In step S2, the MFP 300 requests, from the document distributing apparatus 500, the patient information, the document information, the document name extraction region setting information, and the doctor information. At step S3, the document distributing apparatus 500 sends the patient information, the document information, the document name extraction region setting information, and the doctor information to the MFP in response to the request.

The processes from step S4 to step S6 are the same as the processes from step 4 to step S6 in FIG. 12. At step S7-1, the extracting unit 353 of the MFP 300 extracts image data corresponding to the first extraction region from the scanned image data.

At step S7-2, the extracting unit 353 extracts image data corresponding to the second extraction region including the entry field of the doctor's signature from the scanned image data. The process of step S8-1 is the same as the process of step 8 in FIG. 12.

At step S8-2, the MFP 300 determines the presence or absence of entry of the doctor's signature. When the MFP 300 determines that there is an entry of the patient signature at step S8-1 and no entry of the doctor signature at step S8-2, the user, such as a staff person at the MFP 300, confirms the patient signature to output the scanned image data to the doctor. Then, the doctor receives the scanned image data, not including the doctor signature, and fills in the doctor's signature on the output document. Details of this step will be described below.

When the MFP 300 determines that there is an entry of the patient's signature at step S8-1 and the doctor's signature at step S8-2, the user, such as a doctor, confirms the doctor's signature, and the scanned image data is sent to the document management apparatus 600 via the document distributing apparatus 500. The document management apparatus 600 registers the scanned image data. Details of this step will be described below.

When the MFP 300 determines that there is no entry of the patient's signature at step S8-1 and the doctor's signature at step S8-2, the displaying unit 352 of the MFP 300 displays a screen to notify an error message to the user.

<In Case that the Patient Signature is Present and the Doctor Signature is Absent>

The processes from step S9a to step S12a are the same as the processes from step S9 to step S12 in FIG. 12. At step S13a, the connection unit 351 sends, to the document distributing apparatus 500, the scanned image, the patient ID corresponding to the patient selected by the user based on the patient signature, and the doctor ID identifying the doctor corresponding to the selected patient in the patient information.

At step S14a, the connection unit 551 receives the scanned image, the patient ID, and the doctor ID from the MFP 300, and registers a set of the received patient ID and the received doctor ID in the doctor's waiting list. The processes from step S15a to step S17a are the same as the processes from step S14 to step S16 in FIG. 12.

<In Case that the Patient and Doctor Signatures are Present>

At step S9b, the connection unit 351 requests the doctor's waiting list to the document distributing apparatus 500. The connection unit 551 sends the doctor's waiting list to the MFP 300 in response to the request from the MFP 300 (Step S10b).

At step S11b, the screen generating unit 357 generates a confirmation screen shown in FIG. 17, and the displaying unit 352 displays the confirmation screen. The confirmation screen including the image of the patient's signature, the image of the doctor's signature, and a list of one or more sets of the patient's name and the doctor's name. All of the sets of the doctor and patient in the doctor's waiting list are included in the displayed list.

At step S12b, the user, such as the doctor at the MFP 300, recognizes a set of the patient and doctor corresponding to the patient's signature and doctor's signature, selects the set of the patient and doctor from among the list, and pushes the "OK" button. If the user cannot find an appropriate set from the displayed list, he pushes the "cancel" button.

At step S13b, the connection unit 351 sends the scanned image, the selected patient ID, and the selected doctor ID to the document distributing apparatus 500. At step S14b, the connection unit 551 deletes a set of the received patient ID and the received doctor ID from the doctor's waiting list.

At step S15b, the connection unit 551 sends the scanned image, the document identification information, such as the document name or document type, and patient identification information, such as the patient ID, to the document management apparatus 600 and requests registration of the scanned image data. At step S16b, the document management apparatus 600 registers the scanned image associated with the document identification information and patient identification information in a storage of the document management apparatus 600.

It should be noted that each operation by each functional unit configuring the information processing system according to the present embodiments is executed by programs implemented on a computer. The CPU 301 and 501 (processing circuitry) load a program stored in the ROM 302 and 502 respectively. Then, each process is executed based on the programs.

An information processing system, an information processing apparatus such as an image forming apparatus, a document distributing apparatus, and a document management apparatus according to the embodiments of the present disclosure are described above. However, embodiments in accordance with this application may include variations and modifications made without departing from the scope of this application. For example, circuitry of an information processing system, a user terminal, and a data processing system may execute a method in accordance with the present disclosure.

The functions and features described herein may also be executed by various distributed components of a system. For example, one or more processors may execute these system functions, wherein the processors are distributed across multiple components communicating in a network. The distributed components may include one or more client and server machines, which may share processing in addition to various human interface and communication devices (e.g., display monitors, smart phones, tablets, and PDAs).

Moreover, embodiments in accordance with the present disclosure may utilize circuitry, dedicated hardware, or a mixture of dedicated hardware and and/or circuitry executing software. For example, the present disclosure may be implemented as one or more networked processing apparatuses including circuitry that executes software in accordance with the present disclosure. Processing apparatuses in accordance with the present disclosure may comprise any suitably programmed apparatuses, such as a general purpose computer, personal digital assistant, mobile telephone (such as a WAP or 3G-compliant phone) or other digital device including circuitry.

Aspects of the present disclosure may encompass computer software that is executed by circuitry, processing circuitry, or another programmable device. The computer software may be provided to the programmable device using any storage medium for storing processor readable code such as a floppy disk, hard disk, CD-ROM, magnetic tape device, solid state or other memory device.

What is claimed is:

1. An information processing apparatus, comprising: circuitry configured to acquire an image of a document; extract a first part of the acquired image based on a first extraction region setting stored in a memory; and display a selection screen including the first part of the acquired image and a user list including one or more users, wherein the first part of the acquired image allows a user to recognize a first user indicated by the first part of the acquired image, and the user list allows the user to select the first user, wherein the circuitry is further configured to display the user list including one or more sets of the first user and a second user, and output the acquired image of the document for the second user corresponding to the selected first user in the set including the user list.

2. The information processing apparatus as claimed in claim 1, wherein the circuitry is further configured to acquire the user list based on a user attribute, the user attribute being specified based on the document, and display the selection screen including the acquired user list.

3. The information processing apparatus as claimed in claim 2, wherein the circuitry is further configured to acquire document type identification information included in the acquired image of the document;
   specify, based on the acquired document type identification information, the user attribute used for acquiring the user list, wherein one of a plurality of user attributes and one of the document type identification information are associated with each other.

4. The information processing apparatus as claimed in claim 1, wherein the circuitry is configured to display the selection screen including a second part of the acquired image based on a second extraction region setting stored in the memory, wherein the second part of the acquired image allows the user to recognize the second user indicated by the second part of the acquired image, and the user list allows the user to select the first user.

5. The information processing apparatus as claimed in claim 4, wherein the circuitry is further configured to determine whether there is an entry or not for each of the first and second parts of the acquired image; and
   output the acquired image data to output a destination determined based on a determination of a presence or absence of the entry for each of the first and second extraction regions.

6. An information processing system, comprising:
   a memory to store a first extraction region setting; and
   circuitry configured to acquire an image of a document;
   extract a first part of the acquired image based on the first extraction region setting; and
   display a selection screen including the first part of the acquired image and a user list including one or more users, wherein the first part of the acquired image allows a user to recognize a first user indicated by the first part of the acquired image, and the user list allows the user to select the first user, wherein
   the memory stores device information associated with a second user with an output destination, and
   the circuitry is further configured to
      display the user list including one or more sets of the first user and second user, and
      output the acquired image of the document to the output destination associated with the second user corresponding to the selected first user in the one or more sets included in the user list.

7. The information processing system as claimed in claim 6, wherein the circuitry is further configured to acquire the user list based on a user attribute, the user attribute being specified based on the document, and display the selection screen including the acquired user list.

8. The information processing system as claimed in claim 7, wherein the memory stores document information associating one of a plurality of user attributes with one of document type identification information; and the circuitry is further configured to acquire the document type identification information included in the acquired image of the document; and
   specify, based on the acquired document type identification information and the stored document information, the user attribute used for acquiring the user list.

9. The information processing apparatus as claimed in claim 6, wherein the circuitry is further configured to display the selection screen including a second part of the acquired image based on a second extraction region setting stored in the memory, wherein
   the second part of the acquired image allows the user to recognize the second user indicated by the second part of the acquired image, and the user list allows the user to select the first user.

10. The information processing apparatus as claimed in claim 9, wherein the circuitry is further configured to
    determine whether there is an entry or not for each of the first and second parts of the acquired image; and
    control to output the acquired image data for one of printing at a print device and registering in a storage device, based on a determination of a presence or absence of the entry for each of the first and second extraction regions.

* * * * *